United States Patent [19]

Weinberg

[11] 3,956,692

[45] May 11, 1976

[54] METAL OBJECT COMPARATOR UTILIZING A RAMP HAVING A V-SHAPED SLOT FOR MOUNTING THE OBJECT ACCURATELY WITHIN THE TEST COIL

[75] Inventor: Stanley Weinberg, Los Angeles, Calif.

[73] Assignee: Wein Products, Inc., Los Angeles, Calif.

[22] Filed: Dec. 23, 1974

[21] Appl. No.: 535,858

[52] U.S. Cl. .............................. 324/34 R; 324/41; 194/100 R
[51] Int. Cl.² .................. G01R 33/12; G07F 3/02
[58] Field of Search ................... 324/34 R, 40, 41; 194/100 R, 100 A, 101

[56] References Cited
UNITED STATES PATENTS

| | | | |
|---|---|---|---|
| 2,331,418 | 10/1943 | Nolde | 324/34 R |
| 3,686,563 | 8/1972 | Walter | 324/34 R |

FOREIGN PATENTS OR APPLICATIONS

| | | | |
|---|---|---|---|
| 255,556 | 3/1964 | Australia | 324/41 |

*Primary Examiner*—Robert J. Corcoran
*Attorney, Agent, or Firm*—Edward A. Sokolski

[57] ABSTRACT

A radio frequency oscillator circuit has its tuning circuit coil mounted so as to conveniently receive an object to be tested in preselected precisely defined positions proximate to the windings thereof. A "standard" metal object is placed in a predetermined position proximate to the coil windings and the oscillator activated. The output of the oscillator is detected to produce a DC which is a function of the size, shape, specific gravity and metallic content of the piece being tested. This DC output is amplified and fed to a meter. A nulling circuit is utilized to "null" the meter circuit with the "standard" or reference object in position proximate to the oscillator coil. An object to be tested is then placed proximate to the coil in precisely the same position that was formerly occupied by the "standard" and the meter observed for deviations from the "null" position. If the object to be tested is identical or closely similar in size, shape, specific gravity and metallic content to the reference, the meter deviation will be within predetermined acceptable limits, in view of the fact that the tuning of the oscillator is dependent on the size, shape, specific gravity and metallic content of the objects within the coil which affect hysteresis and eddy current losses thereof, and thus the "Q" of the circuit.

5 Claims, 4 Drawing Figures

METAL OBJECT COMPARATOR UTILIZING A RAMP HAVING A V-SHAPED SLOT FOR MOUNTING THE OBJECT ACCURATELY WITHIN THE TEST COIL

This invention relates to a device for determining the weight and metallic content of metal objects as compared with a standard reference object, and more particularly to such a device which utilizes an electronic detection circuit in its implementation.

In evaluating precious metal objects, such as gold and silver coins, bullion pieces, etc., it is important to accurately verify the specific gravity, size, shape and metallic content of the object to obtain a proper value appraisal. Many testing devices of the prior art have relied almost solely on weighing and displacement and have made alloy appraisals in a rather cursory manner by physical examination and rough chemical and hardness tests. Especially in situations where a number of metal pieces have to be checked fairly rapidly, it is difficult to make accurate evaluations of metallic content with the techniques of the prior art.

The present invention overcomes the aforementioned prior art shortcomings in providing means for accurately and rapidly checking the specific gravity, size, shape and metallic content (alloy) of objects to be tested. This end result is achieved by comparing the electrical characteristics of the object to be tested with those of a "standard" or reference object in an electrical testing circuit. The electrical circuit utilized is highly accurate in its measuring characteristics, such that very slight variations in the characteristics of the tested object from the "standard" are immediately apparent to the operator. Further, the device of this invention is very simple to operate, even for a relatively inexperienced operator, and requires a few simple, easily learned operations which can be performed with the exercise of a minimum amount of skill.

It is therefore an object of this invention to provide an improved detector for determining the specific gravity, size, shape and metallic content of a metallic object as compared with a standard.

It is a further object of this invention to provide a device for evaluating the specific gravity, size, shape and metallic content of objects which rapidly provides a highly accurate readout indicating such characteristics as compared with those of a standard object.

It is a further object of this invention to provide a device for determining the specific gravity, size, shape and metallic content of objects which requires a minimum of skill and experience to operate.

Other objects of this invention will become apparent as the description proceeds in connection with the accompanying drawings, of which:

Briefly described, the device of the invention is as follows: A high "Q" radio frequency oscillator circuit has its coil mounted to receive, in a preselected precisely defined position in proximity to the windings thereof, standard reference objects and objects to be tested. The output of the oscillator is detected to provide a DC signal which is fed to an amplifier and null adjust circuit, the output of the amplifier being fed to a meter. A standard or reference object is placed in a predetermined precisely defined position in proximity to the windings of the oscillator coil such as to cause eddy current and hysteresis losses of the coil and thus lower the "Q" of the circuit. With the standard piece so positioned, the meter is "nulled". The standard object is then removed from the coil and the object to be tested which appears to be the same as the standard is placed in the exact same position previously occupied by the standard. Deviation of the meter needle from the null position is noted and if beyond predetermined limits, the tested object is rejected as not being up to the standard set by the "reference", this in view of the fact that the tuning characteristics of the oscillator have been changed by virtue of the change in the coil losses and thus the "Q" of the circuit.

Figure 1:
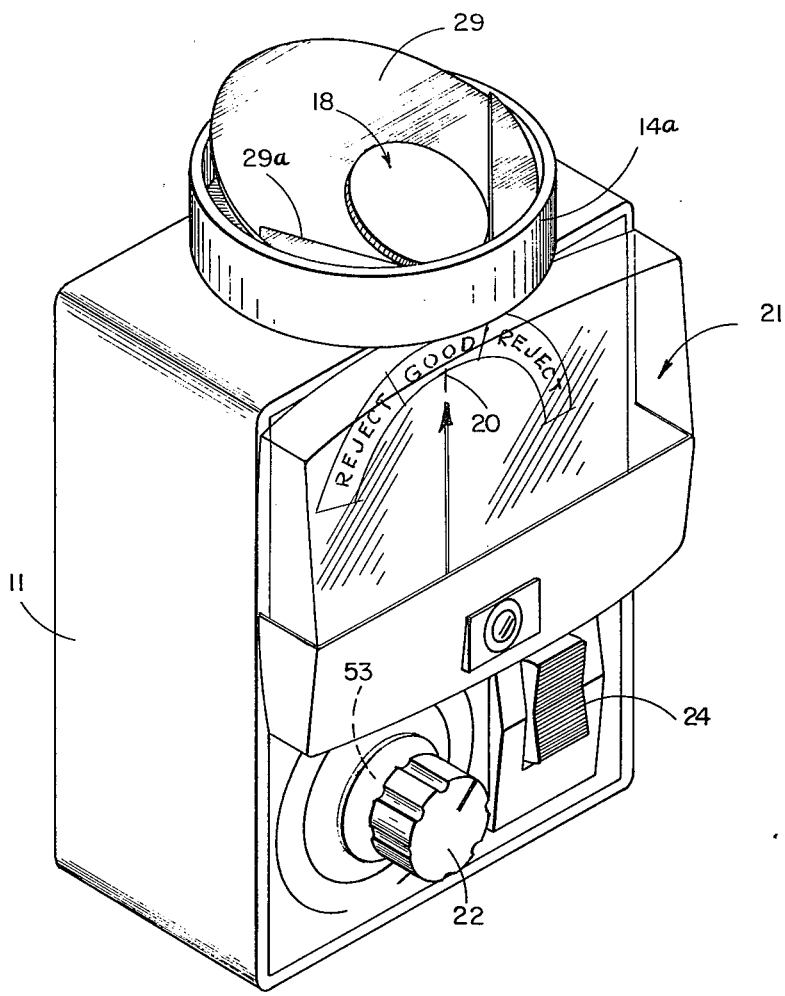
FIG. 1 is a perspective view illustrating a preferred embodiment of the invention in operation.
Figure 2:
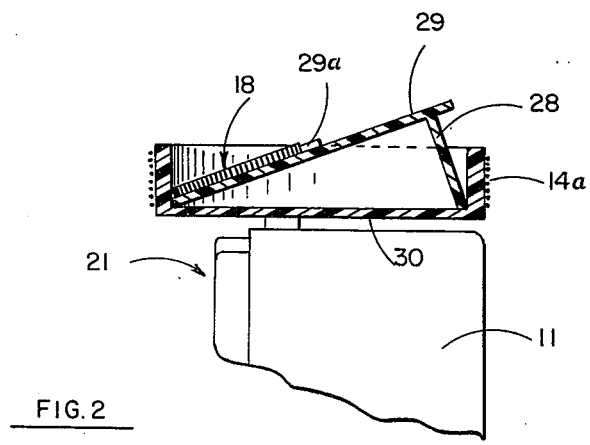
FIG. 2 is a side elevational view partially in section of the oscillator testing coil of the preferred embodiment.

Referring now to FIGS. 1 and 2, a perspective pictorial view and a functional schematic of a preferred embodiment of the invention are respectively shown. As can be seen in FIG. 1, sensing coil 14a is open wound (ie., has an air core) and is mounted on the top of instrument casing 11. Positioned within sensing coil 14a is a ramp 29 with a "V" slot 29a formed therein. Ramp 29 is supported by means of slanted base 28 on tray 30 which forms a bottom for the coil form. This "V" slot 29a is utilized to place an object such as coin 18 to be tested and a standard object purportedly having the same characteristics both in precisely the same position. It is to be noted that the "V" slot permits smaller diameter coins to come closer to the coil windings than larger diameter coins, thereby tending to equalize the relative effect on the circuit for different size coins. Instrument casing 11 also supports galvanometer 21 and nulling potentiometer 53 which is adjusted by means of knob 22. Also supported on casing 11 is switch 24 which is used to turn the instrument "ON" and "OFF" and to the "BATTERY TEST" position. Casing 11, ramp 29, base 28 and tray 30 are of a dielectric material such as a suitable plastic.

Figure 3:
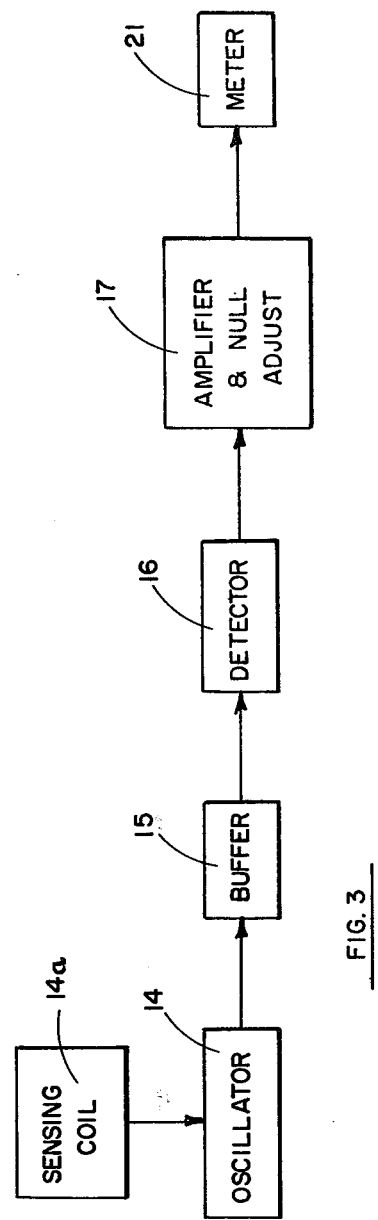
FIG. 3 is a functional block diagram of the circuitry of the preferred embodiment.

Housed within casing 11 is circuitry as now to be described in connection with FIGS. 3 and 4. Referring particularly to FIG. 3, sensing coil 14a serves as the tuning coil for oscillator 14. Oscillator 14 may be of the Colpitts variety and may operate at a radio frequency of the order of approximately 1 megaHertz. This oscillator is designed to have very low power output and a high "Q". The output of oscillator 14 is fed to buffer stage 15 and from the buffer to RF detector 16, the buffer operating to isolate the oscillator from any loading effects of the detector. The output of detector 16 is a DC voltage and is fed to amplifier and null adjust circuit 17. The null adjust circuit, as to be explained more fully in connection with FIG. 4, is operated to adjust the output of the amplifier to meter 21 with a "standard" object positioned in the sensing coil so as to provide a "null" reading on the meter.

In operating the instrument, a standard object 18 which may be a gold coin, is placed in a predetermined position proximate to coil 14a, for example lying flat on the ramp 29 with its rim against "V" slot 29a. Switch 24 is then thrown to the "ON" position to provide electrical power to the circuitry of FIG. 3. 30 to 60 seconds are allowed for circuit stabilization. Knob 22 is then rotated (thereby rotating the arm of potentiometer 53) until the needle of meter 21 is centered as shown in FIG. 1. The presence of coin 18 proximate to the coil, of course, will change the "Q" and the tuning characteristics of the oscillator circuit. The "standard" coin 18 is then removed and a coin purportedly of identical characteristics is placed in the exact same position that it occupied within the "V" slot 29a. The needle of meter 21 is then observed. If it falls in the "good" region of the indicator panel, then it is acceptable. If it falls in either of the "reject" areas or off scale, then it is unacceptable. Thus, if the coin being tested varies either in size, shape, specific gravity or metallic content from the standard beyond a predetermined acceptable range, the meter will accurately indicate such condition.

Figure 4:
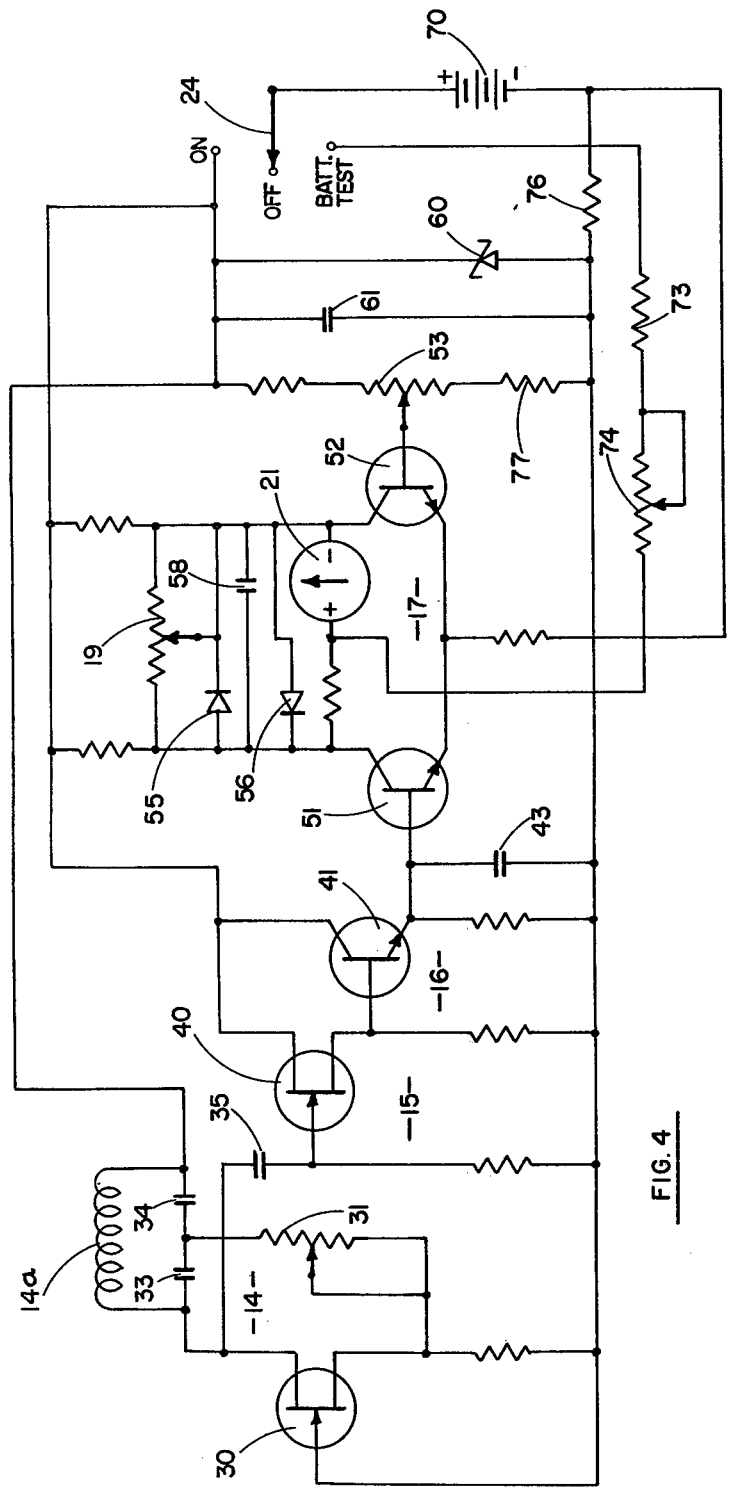
FIG. 4 is a schematic drawing of the circuitry of the preferred embodiment.

Referring now to FIG. 4, the circuitry used in the preferred embodiment of the device of the invention is schematically illustrated. Oscillator 14 is a Colpitts oscillator employing FET 30. The amplitude of oscillation is controlled by means of potentiometer 31 which is connected in the feedback circuit between the source of the FET and the common connection between capacitors 33 and 34. The tuning circuit of the oscillator is formed by sensing coil 14a and capacitors 33, 34, connected in series with each other between the ends of the coil. The output of oscillator 14 is fed through capacitor 35 to FET 40 which forms a buffer for isolating the oscillator from loading effects which might be presented by detector 16. The output of the buffer is fed to detector 16 formed by transistor 41 connected in emitter-follower configuration, capacitor 43 serving as the RF filter capacitor for the detector. The output of detector 16 is fed to amplifier and null adjust circuit 17. This circuit includes a DC amplifier formed by a pair of transistors 51 and 52 connected in a differential mode with a common emitter resistor. The output of the detector is fed to the base of transistor 51. The base of transistor 52 receives a DC voltage which originates from power source 70 and is determined by the setting of potentiometer 53. Transistor 52 thus provides a reference potential to one side of meter 21. Potentiometer 53 is utilized to "null" meter 21, i.e., to bring the meter to its mid-scale position (indicated by line 20 in FIG. 1) with a standard piece in the sensing coil. It should be immediately apparent that this condition will be reached for any given output of transistor 51 with a particular setting of potentiometer 53 which controls the output of transistor 52. Thus, if the output of transistor 51 changes due to a change in the output of the oscillator occasioned by a difference in the conduction (and eddy currents) of the piece placed in the sensing coil from the standard, meter 21 will no longer be "nulled" with the previous setting of potentiometer 53. Potentiometer 19 is an adjustable shunt across the meter and is used to pre-adjust (factory adjustment) the sensitivity of the meter to provide the desired response. Diodes 55 and 56, which are preferably silicon diodes which do not conduct until there is 0.6 volts thereacross, are used to provide overload protection for the meter movement. Capacitor 58 is used to bypass any stray RF which may appear across the meter movement.

Power is supplied for the circuits from power source 70 when switch 24 is thrown to the "ON" position. A zener diode 60 is provided to assure that the output of power source 70 remains fixed. Capacitor 61 is utilized as an RF filter to keep signals from oscillator 14 from entering the power source.

To assure proper operation of the device, the output voltage of battery 70 is tested by throwing switch 24 to the "BATT. TEST" position which places the output of the battery across meter 21 through resistor 73 and potentiometer 74 and resistors 76 and 77, potentiometer 53 and transistor 52. Potentiometer 74 is adjusted so that meter 21 provides a proper output when the voltage output of the battery is within an acceptable range.

The device of this invention thus provides a simple to operate, yet highly accurate and sensitive means for indicating whether or not a metal piece has acceptable specific gravity, size, shape and metallic characteristics.

While the invention is described and illustrated in detail, it is to be clearly understood that this is intended by way of illustration and example only and is not to be taken by way of limitation, the spirit and scope of the invention being limited only by the terms of the following claims.

I claim:

1. A device for determining the characteristics of a metal object to be tested by comparison with a standard metal object, comprising:
   a radio frequency oscillator, said oscillator including an open wound air core sensing coil in its tuning circuit,
   means for mounting said sensing coil to removably receive said objects in a predetermined position in proximity to the windings thereof, said mounting means comprising a ramp mounted in the core of the sensing coil, said ramp having a "V" slot for receiving the objects,
   detector means for receiving the output of said oscillator and providing a DC in accordance with said oscillator output,
   amplifier means for amplifying the output of said detector means,
   indicator means for receiving the output of said amplifier means, and
   null circuit means for adjusting the current fed to said indicator means to provide a predetermined "null" reading thereon when said standard object is in said predetermined position in close proximity to the coil windings,
   whereby when said object to be tested is placed in said predetermined position after said null circuit has been adjusted to said standard object, deviations of the indicator reading from the "null" reading are indicative of the characteristics of the object to be tested as compared with the standard object.

2. The device of claim 1 wherein said means for mounting the coil comprises a casing for the device, said coil being mounted on the top surface of said casing with the windings of the coil running substantially parallel to said surface.

3. The device of claim 1 wherein said indicator is a galvanometer.

4. A device for determining the characteristics of a metal object to be treated by comparison with a standard metal object comprising:
   a casing,
   a radio frequency oscillator, said oscillator including an open wound air core sensing coil in its tuning circuit, said sensing coil being mounted on a surface of said casing, detector means for receiving the output of said oscillator and providing a DC in accordance with the oscillator output, amplifier means for amplifying the output of said detector means, a galvanometer mounted on said casing for receiving the output of said amplifier means, means located in the air core of said sensing coil for use in positioning the object to be tested and the standard object at the same predetermined position in said core comprising a tray attached to the bottom of the coil, a ramp extending angularly upward from said tray and having a V-shaped slot formed therein for receiving the objects, and null circuit means for adjusting the current fed to said galvanometer to provide a predetermined "null" reading thereon when the standard object is in said predetermined position in said sensing coil core, whereby after the null circuit has been adjusted with the standard object in position, the object to be tested is placed in said predetermined position, deviations of the galvanometer reading from the "null" reading being indicative of the characteristics of the object to be tested as compared with the standard object.

5. The device of claim 4 wherein the sensing coil is mounted with the windings thereof substantially parallel to said casing surface.

* * * * *